US012752097B2

(12) United States Patent
Lauren et al.

(10) Patent No.: US 12,752,097 B2
(45) Date of Patent: Oct. 6, 2026

(54) PRECISION-CONTROLLED CONDUIT RESTRICTION DEVICE

(71) Applicant: Renal Devices Inc., Buffalo, NY (US)

(72) Inventors: Mark D. Lauren, Amherst, NY (US); Daniel D'Arcy, Orchard Park, NY (US)

(73) Assignee: Renal Devices Inc., Buffalo, NY (US)

( * ) Notice: Subject to any disclaimer, the term of this patent is extended or adjusted under 35 U.S.C. 154(b) by 314 days.

(21) Appl. No.: 18/443,726

(22) Filed: Feb. 16, 2024

(65) Prior Publication Data

US 2025/0262422 A1 Aug. 21, 2025

(51) Int. Cl.

*A61M 1/36* (2006.01)
*A61M 39/28* (2006.01)
*A61M 39/22* (2006.01)

(52) U.S. Cl.

CPC .......... *A61M 39/28* (2013.01); *A61M 1/3661* (2014.02); *A61M 2039/226* (2013.01); *A61M 2205/0238* (2013.01); *A61M 2205/32* (2013.01); *A61M 2205/583* (2013.01)

(58) Field of Classification Search

CPC ................ A61M 39/28; A61M 1/3661; A61M 2039/226; A61M 1/3655; A61M 39/281; A61M 2039/282; A61M 39/283; A61M 39/284; A61M 39/286; A61M 39/285; A61M 39/287; A61M 39/288; A61B 17/12; A61B 17/122; A61B 17/132; A61B 17/1355; A61B 17/1327; A61B 17/1322; A61B 17/12009; A61B 17/12013; A61B 17/12036; A61B 17/1204; A61B 2017/12018; A61B 2090/061; A61B 17/1285; A61B 2017/00641; A61B 17/0057; A61B 2017/1107; A61B 5/026; A61B 8/0891

See application file for complete search history.

(56) References Cited

U.S. PATENT DOCUMENTS

| | | | | |
|---|---|---|---|---|
| 5,910,149 | A * | 6/1999 | Kuzmak | A61F 5/0066 606/151 |
| 9,241,717 | B2 | 1/2016 | Gettman | |
| 9,295,774 | B2 | 3/2016 | Claude et al. | |
| 9,393,026 | B2 | 7/2016 | Cully | |
| 9,662,117 | B2 | 5/2017 | Forsell | |
| 9,730,698 | B2 | 8/2017 | Cazenave | |

(Continued)

*Primary Examiner* — Tan-Uyen T Ho
*Assistant Examiner* — Bridget E. Rabaglia
(74) *Attorney, Agent, or Firm* — Law Office of Vincent LoTempio PLLC; Vincent G. LoTempio; Robert L. Cerasa

(57) ABSTRACT

The invention relates to a device for providing controlled restriction of a hollow conduit in a body. The device may include a band element having a tunnel section with a proximal opening and a distal opening. The device may further include a length of the band extending from the proximal opening. The device may further include a controller, removably connected to the distal opening, comprising an adjusting mechanism for changing a diameter of the band. The end of the band may be insertable through the proximal opening to form a loop around a hollow conduit, and the end of the band length may be advanced into the controller to permanently engage with the adjusting mechanism. After adjusting the diameter of the band, the band may be secured and the controller disconnected, leaving the band and securing means around the hollow conduit.

16 Claims, 14 Drawing Sheets

(56) References Cited

U.S. PATENT DOCUMENTS

| | | | | |
|---|---|---|---|---|
| 2019/0321607 | A1* | 10/2019 | Pai | A61M 29/00 |
| 2019/0336675 | A1* | 11/2019 | Lauren | A61B 17/12013 |
| 2021/0283302 | A1* | 9/2021 | Hall | A61L 27/16 |

* cited by examiner

PRECISION-CONTROLLED CONDUIT RESTRICTION DEVICE

TECHNICAL FIELD

Generally, the invention relates to the field of vascular access and blood flow regulation, and more particularly, to a device that is designed to controllably band blood conduits, thereby facilitating stable and precise control over blood flow rates within these conduits.

BACKGROUND

Kidney failure due to chronic kidney disease or diabetes compels individuals to begin dialysis as a substitute for kidney function. A significant majority, approximately 90%, opt for hemodialysis, undergoing three sessions per week. To facilitate the required blood flow for the dialysis machinery, the preferred approach is the creation of an arteriovenous (AV) access. This access may be achieved through a natural vein or a vascular graft, both collectively referred to here as a "fistula." Functionally, a fistula requires specific attributes, such as a blood flow of around 500 ml/min, a diameter of 5-6 mm, and the ability to sustain cannulation for dialysis access three times a week.

However, some patients experience an escalating blood flow through the fistula, which leads to ischemia and cardiac complications. In certain cases, the flow may reach 2-3+ liters/minute, a significant fraction of the cardiac output. Addressing such high flow becomes imperative to prevent issues ranging from cold extremities to high-output heart failure. Clinical methods to reduce AV fistula flow are in place, which include vessel surgeries and banding of the fistula.

Vessel surgeries generally redirect a portion of the incoming blood to the fistula through various techniques. However, these procedures lack precise control over the final flow, and come with associated challenges, morbidity, and costs. The adequacy of flow reduction usually relies on surgical judgment based on visual indicators like color and pulse return. Vascular surgical flow reduction does not significantly affect peripheral resistance.

Banding involves directly reducing the diameter of the fistula, which has the effect of increasing peripheral resistance. As a result, banding can potentially alleviate both ischemic and cardiac symptoms. Existing banding techniques include plication, MILLER banding, and applying fabric cuffs around the fistula.

Some devices have been developed to restrict the diameter of fistulas. One prior art device for restricting fistulas is described in U.S. Patent Application US20190336675-A1 (hereinafter the '675 device). The '675 device discloses an adjustable band and a disposable delivery system for banding blood conduits. The band is connected to a female connector at one end and a controlling mechanism on the other. The male connector houses a catheter that is used to draw-in the band when adjusting the band diameter. The band is secured by a lock that cinches a sleeve over the catheter.

However, the '675 device has significant limitations regarding clinical safety and convenience that render it clinically and commercially unviable. Some of these limitations are:

The '675 device requires a hard plastic component, female connector, to be attached to the end of the band. Leading this small component around a vessel requires care and skill. Further, it requires a precise orientation to attach the female connector to the male connector. This step involves manipulating small plastic parts in a surgical field, which may be awkward and difficult. Moreover, this snap-together connection is made at or near the outside surface of the vessel, which may potentially pinch the vessel when the two parts are brought together.

The device also requires a secondary securing of the snapped-together pieces, to be performed by wrapping and tying-off suture around annular grooves on the connectors. This is an extra and inconvenient procedure.

Further, the band of the device creates a pinch point on the outside of the vessel as the band is drawn into the catheter inside the male connector during band closure. The pinching is caused by having an open gap between the outer vessel wall, band, and the hard stationary faces presented by the male and female connectors. The moving band tends to compress the vessel wall against these faces, which can damage the vessel wall and lead to thrombosis.

In addition, the band has a segment that consists of a fixed piece of plastic with a fixed curvature, female connector. This creates a physical discontinuity in the band and prevents it from ever being circular. Also, the fixed end of band is bonded into a bushing, which is then bonded into female connector. As a result, the band exits the female connector at a fixed angle, which contributes to the non-circular nature of the band.

Furthermore, the device requires implanting adhesive that is used in three locations: bonding the fixed end of the band to a bushing, bonding the bushing to female connector, and bonding catheter to male connector. Implanting adhesive may pose risks of a toxic or allergic reaction.

Therefore, there is a need for an improved device for controllably banding blood conduits that overcomes these limitations and provides stable and precise blood flow control.

Thus, a heretofore unaddressed need exists in the industry to address the aforementioned deficiencies and inadequacies.

SUMMARY OF INVENTION

In one embodiment, a device for providing controlled restriction of a hollow conduit (e.g., vessel) in a body is disclosed. The device may include a band element having a tunnel section with a proximal opening and a distal opening. The device may further include a length of band extending from the proximal opening. The end of the band may be connected to a controller to adjust the diameter of the band. The device may further include the controller comprising an adjusting mechanism for changing a diameter of the band element. The end of the band may be insertable through the proximal opening to form a loop around the hollow conduit, and the end of the band may be advanced into the controller to permanently engage with the adjusting mechanism.

In another embodiment, a device for providing controlled restriction of a hollow conduit (e.g., vessel) in a body is disclosed. The device may include a band element having a tunnel section with a proximal opening and a distal opening. The device may further include a length of the band extending from the proximal opening. The free end of the band may be insertable through the proximal opening to form a loop around the hollow conduit, and the end of the band may be further advanced into the controller to permanently engage with an adjusting mechanism. The device may further include periodically spaced elements on the band acting as detents when passing through the tunnel section. The device may further include an adjusting mechanism within the controller for changing the diameter of the band.

In yet another embodiment, a device for providing controlled restriction of a hollow conduit in a body is disclosed. The device may further include a band element having a tunnel section with a proximal opening and a distal opening. The device may further include a band length extending from the proximal opening. The free end of the band length may be insertable through the proximal opening to form a loop around the hollow conduit, and the end of the band length may be further advanced into the controller to permanently engage with an adjusting mechanism. After adjusting, the band may be secured in place and the controller disconnected, leaving the band and securing means implanted.

It is to be understood that both the foregoing general description and the following detailed description are exemplary and explanatory only and are not restrictive of the invention, as claimed.

BRIEF DESCRIPTION OF THE DRAWINGS

The present application can be best understood by reference to the following description taken in conjunction with the accompanying drawing figures, in which like parts may be referred to by like numerals.

DETAILED DESCRIPTION OF THE DRAWINGS

The following description is presented to enable a person of ordinary skill in the art to make and use the invention, and is provided in the context of particular applications and their requirements. Various modifications to the embodiments will be readily apparent to those skilled in the art, and the generic principles defined herein may be applied to other embodiments and applications without departing from the spirit and scope of the invention.

Exemplary embodiments are described with reference to the accompanying drawings. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims. Additional illustrative embodiments are listed below.

Figure 1:
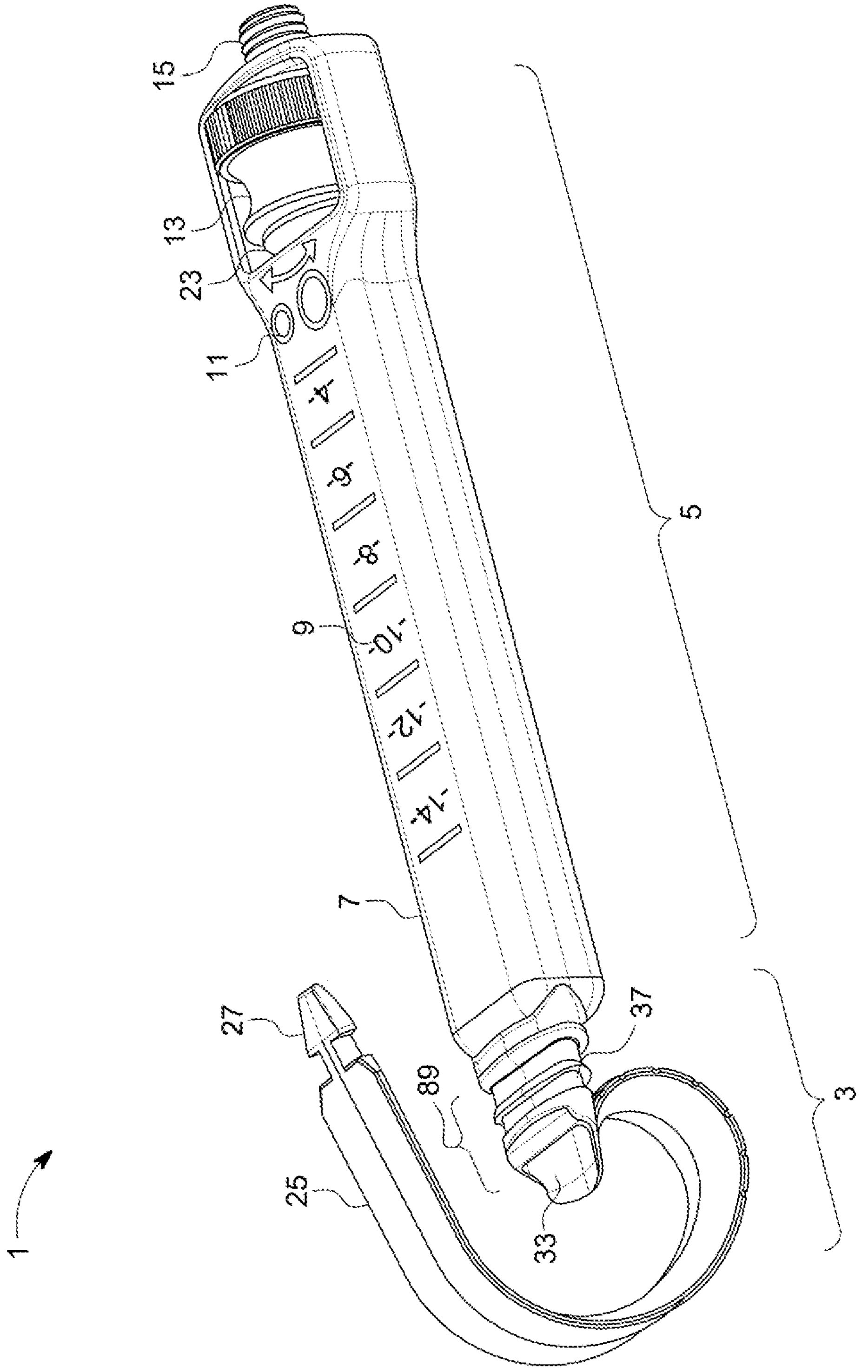
FIG. 1 is a perspective view of a device for providing controlled restriction of a hollow conduit in a body, in accordance with an embodiment of the present disclosure.
Figure 2:
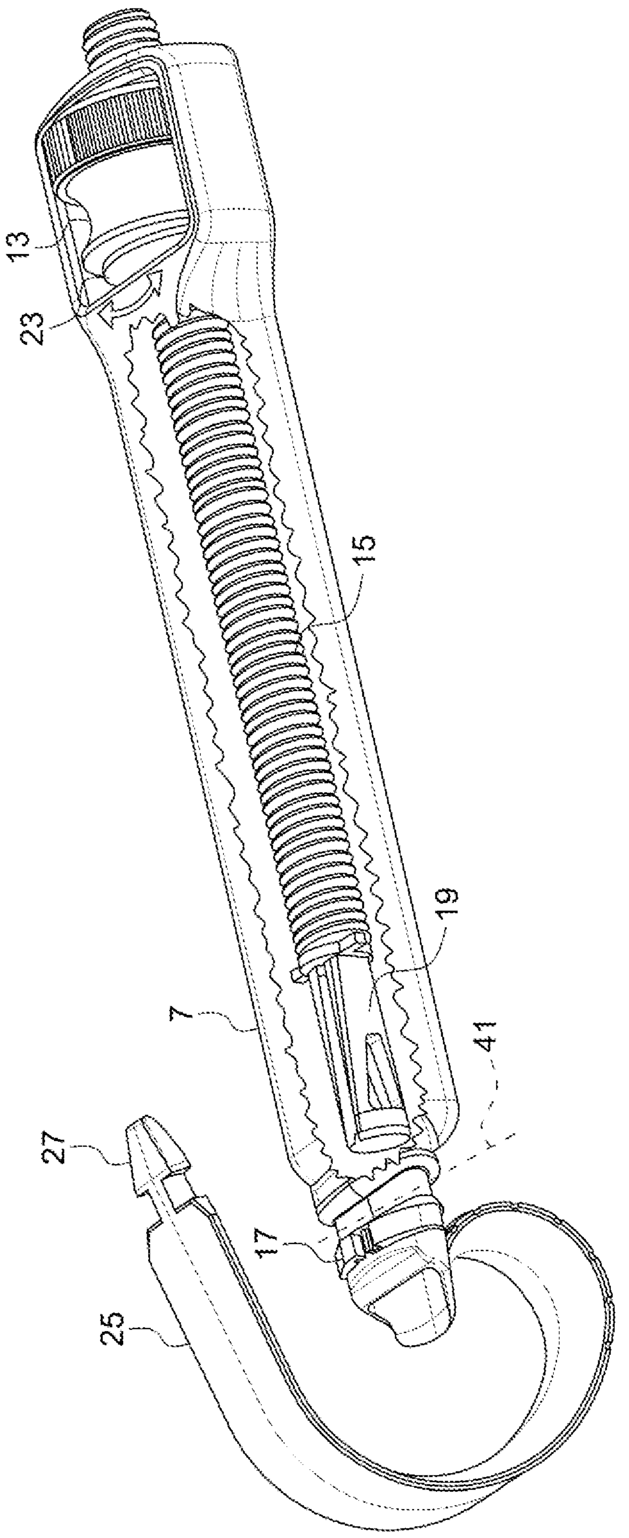
FIG. 2 is a sectional view of the device shown in FIG. 1, in accordance with an embodiment of the present disclosure.
Figure 3:
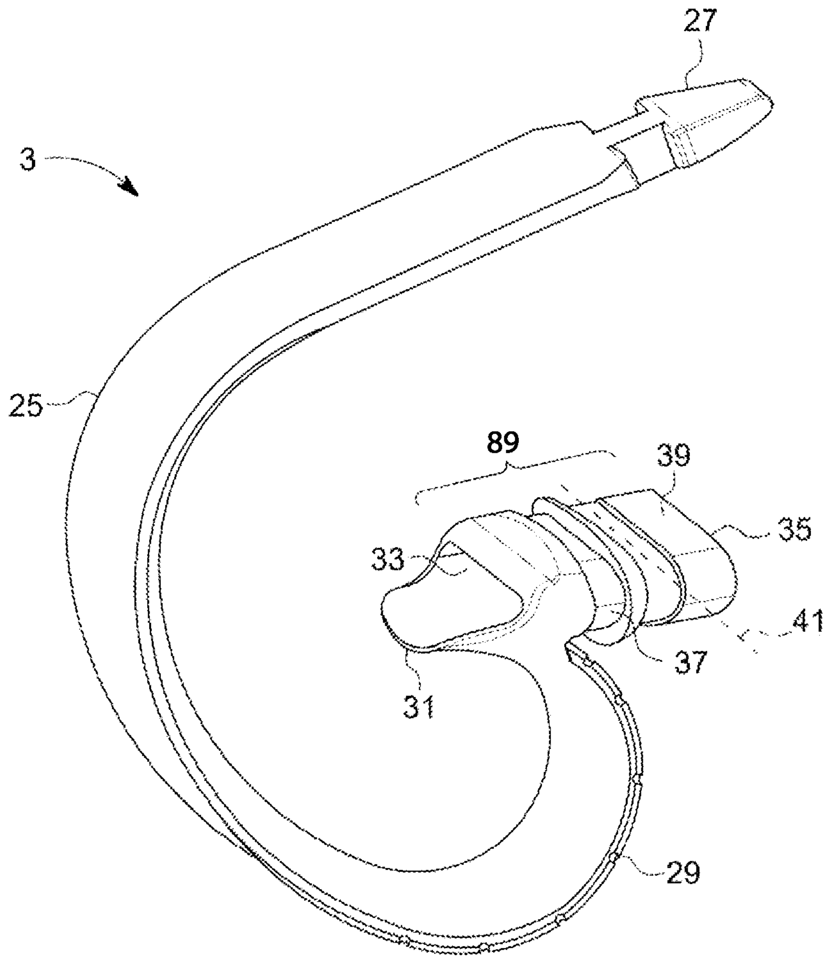
FIG. 3 is a perspective view of a band element, in accordance with an embodiment of the present disclosure.
Figure 4A:
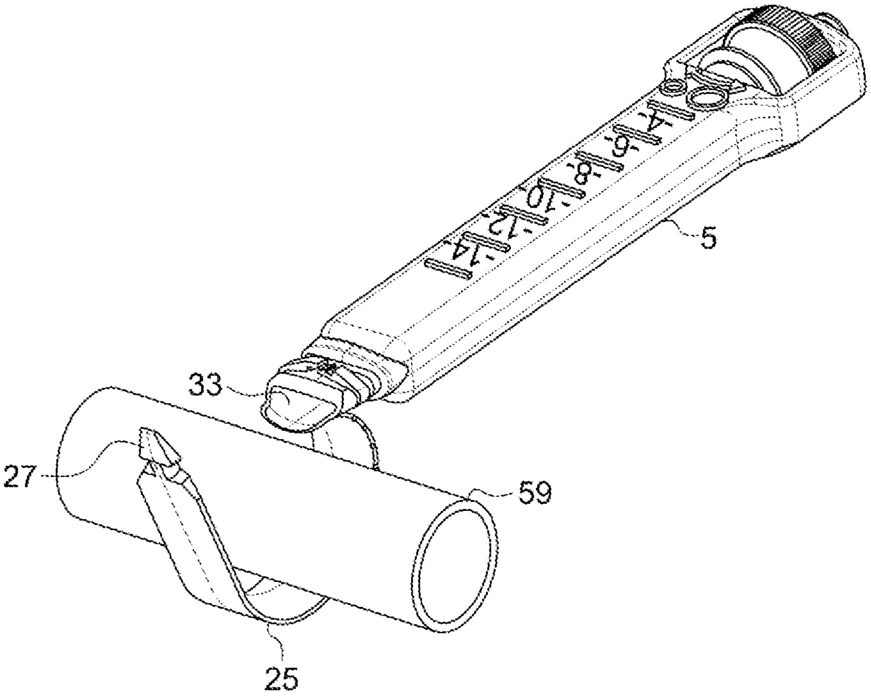
FIG. 4A is a perspective view of the device shown in FIG. 1 in an unsecured state, in accordance with an embodiment of the present disclosure.
Figure 4B:
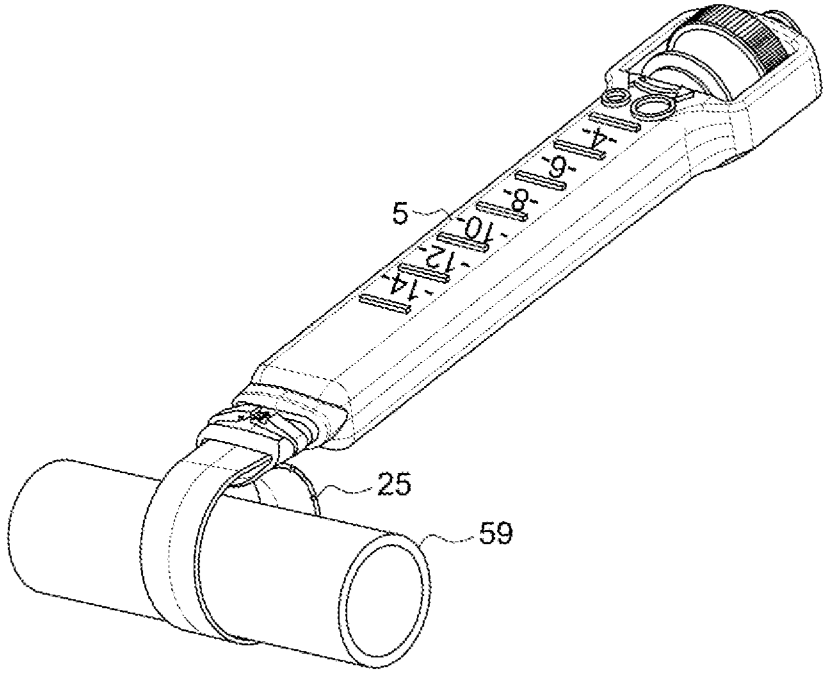
FIG. 4B is a perspective view of the device shown in FIG. 1 in a secured state, in accordance with an embodiment of the present disclosure.

Referring now to figures, FIG. 1 is a perspective view of a precision-controlled conduit restriction device 1 for providing controlled restriction of a hollow conduit in a body. FIG. 2 is a sectional view of the precision-controlled conduit restriction device 1. FIG. 3 is a perspective view of a band element 3. FIG. 4A is a perspective view of the precision-controlled conduit restriction device 1 in an unsecured state. FIG. 4B is a perspective view of the precision-controlled conduit restriction device 1 in a secured state. The following description should be read in view of FIGS. 1-4B.

With reference to FIG. 1, the precision-controlled conduit restriction device 1 may include a band element 3 and a controller 5. The band element 3 has a tunnel section 89 with a proximal opening 33 and a distal opening 35. The controller 5 is removably connected to the distal opening 35. In one embodiment, the controller 5 may be a disposable controller. In another embodiment, the controller may be reusable and not disposable. The reusable controller may be designed to be sterilized between uses, and be reversibly connected to the band element 3.

The band element 3 is depicted as a tubular structure, open at both ends, and possessing unique attributes to enable effective and secure restriction.

In various embodiments, the band element 3 is manufactured using advanced materials that meet stringent biocompatibility and safety standards. To achieve this, the band element 3 may be molded using a specialized flexible biomedical polymer such as a polyurethane or polyurethane copolymer. Furthermore, the durometer of the selected biomedical polymer generally falls within a range of about 60 A to 90 A. This durometer range generally provides an optimal balance between flexibility and structural support, allowing the length of band 25 to be readily looped around a hollow conduit and effectively changed in diameter by a controller 5.

Further, the band 25 may be designed with a cross-sectional shape that reflects its intended functionality. The cross-sectional shape of the band 25 may be circular, rectangular, or specifically tailored to produce a desired restriction pattern. This design flexibility allows the precision-controlled conduit restriction device 1 to accommodate various clinical scenarios and patient needs, and adapting to different anatomical requirements. It should be noted that the band 25 may be of different lengths and cross-sections. For example, for AV fistula banding, the band 25 may typically be 2-10 mm wide and may have an inside diameter of 3.5-25 mm.

In other words, the band 25 used to reduce the flow of blood in an AV fistula may vary in size depending on the specific needs of the patient. The width of the band is typically between 2 and 10 mm, and the inside diameter is typically between 3.5 and 25 mm.

Additionally, the band 25 may be coated with a material to enhance either its biological or mechanical performance, or both. More particularly, the band element may be coated with a material, such as parylene to reduce friction and improve biocompatibility. This coating or covering may serve to promote friction between the band element 3 and the outer surface of the hollow conduit, effectively preventing unwanted migration or slippage.

In some embodiment, the band 25 may be treated or covered with a material to increase the sliding friction (e.g., textile fabrics) between the inside of the band and the blood conduit.

In some embodiments, the length of band (e.g., band 25) may be covered with a textile, such as a knitted polyester, to increase the friction between the band and the vessel.

In some embodiments, the band 25 may also possess radiopaque properties, enhancing its visibility under medical imaging techniques such as X-rays or fluoroscopy. This radiopacity may aid healthcare professionals in tracking and positioning the device during implantation and subsequent monitoring procedures. The addition of radiopacity to the band element 3 ensures enhanced visibility during medical imaging procedures, further contributing to the device's ease of implantation and monitoring.

With reference to FIG. 2, the controller 5 may include a mechanism to adjust the diameter of the band. Receiver component 19 is bonded to screw 15. Screw 15 is threaded through captured adjusting nut 13. Turning adjusting nut 13 moves screw 15 linearly in and out of the controller 5. During installation, the arrowhead 27 at the end of the band 25 is inserted through the proximal opening 33 and advanced to connect with the receiver component 19 inside the controller 5. As a result, turning adjusting nut 13 moves the screw, receiver, and band 25 in and out of the controller 5, thereby changing the band diameter.

The controller 5 may further include a housing 7 which may be made from a transparent material, enabling users to visualize internal components (such as, internal screw 15). Transparent housing 7 has a diameter scale 9 and a turn indicator 11. Turn indicator 11 shows which way to turn the adjusting nut 13 to increase or decrease the diameter of the band 25. The scale 9 is positioned to align with a specific marker, such as the front of the screw 15, providing an indication of the current diameter of the band 25. The fineness of the threads on screw 15 determines the relationship between turning the screw and changing the diameter of the band 25. For a 10-32 thread, four turns of the adjusting nut 13 changes the band diameter by 1 mm.

The controller 5 may further include an adjusting nut 13 (e.g., also referred to as a captured nut), which may be rotated to change the diameter of the band 25 by linearly moving a screw 15 that is attached to the arrowhead 27 via receiver component 19. Changing of the diameter of the band 25 may involve drawing the band 25 into the controller 5 through the operation of the adjusting mechanism.

In some embodiments, the adjusting mechanism for changing the diameter of the band 25, may employ a ratchet mechanism that effectively engages with periodically spaced elements on the band 25. These periodically spaced elements along the band engage with a fixed complementary geometry inside the tunnel section. Further, the periodically spaced elements may serve as a series of detents when the band 25 passes through the tunnel section 89. This arrangement allows for controlled adjustments to the band element's diameter, providing precise customization of the device's restriction capabilities. With sufficiency strong detents, the need for separate securing means may not be required.

To further elaborate, the screw 15 may pass through an O-ring 23 and the adjusting nut 13, which may be captured inside the housing 7. The O-ring 23 may provide for the smooth rotation of the adjusting nut 13 during band closure by providing a low friction surface to the rotating adjusting nut 13. The adjusting nut 13 may include threads that may match with the screw 15 (also referred to as a threaded rod), such that turning the adjusting nut 13 may cause linear movement of the screw 15 and the receiver component 19, which may in turn changes the diameter of the band element 3.

In some embodiments, anti-rotation means may be provided to the screw 15 to prevent it from spinning when the adjusting nut 13 is turned. In some embodiments, the controller 5 may include means to limit a displacement of the band element 3.

The controller 5 may be connected to the band element 3 by inserting the end of the band element 3 into the controller 5 and advancing it until it engages with the adjusting mechanism within the controller 5. This may cause the band element 3 to move into a fully open position.

Further, in some embodiments, the controller 5 may be disconnected from the band element 3 by cutting across a short segment of the band element 3 between the controller 5 and a securing means 17 that may be mounted on the tunnel section 89 of the band element 3. This securing means 17 plays a vital role in maintaining the band element 3 at a desired diameter once it has been adjusted. It ensures the stability of the band diameter under normal clinical conditions.

It should be noted that the securing means 17 of the present disclosure is not necessarily intended to be an absolute lock. Rather, the securing means 17 may be designed to maintain the diameter of the band element 3 under clinical conditions, but may allow it to be released from locking state by a high-pressure balloon placed inside a blood vessel 59. The securing means 17 may be activated by pinching its sides to close over the tunnel section 89, compressing the band element 3 and preventing it from slipping back. The securing means 17 is also smoothly contoured with the band element 3, without creating any sharp edges or protrusions that may damage or pinch a vessel wall.

FIG. 3 shows features of the band element 3. The band element 3 is designed with unique properties that facilitate its interaction with both the tunnel section 89 and the controller 5. As stated earlier, the band element 3 has a tunnel section 89 with the proximal opening 33 and the distal opening 35. The tunnel section 89 may include a ramp 31 extending from the base of the proximal opening 33, which conforms to the inner surface of the band 25 as it closes. The tunnel section 89 may further include a notch 37 for locating the securing means, a bonding surface 39 for connecting to the controller 5, and a cut-off plane 41 for disconnecting the controller 5.

The end of band 25 may be molded or shaped to form a connector, such as arrowhead 27. The band 25 may further include a series of notches 29 across its width, which may reduce the force required to close the band 25 to smaller diameters.

FIG. 4A illustrates how the free end of band 25 is looped around a hollow conduit, such as a blood vessel 59. The arrowhead 27 may then be inserted into the proximal opening 33 of the tunnel section 89. Advancing the band 25 and arrowhead 27 through the tunnel section 89 allows arrowhead 27 to connect the receiver component 19 inside the controller 5. The band 25 is then in the fully open position as shown in FIG. 4B.

By way of an example, consider a scenario where a user wants to use the precision-controlled conduit restriction device 1 to control the flow of blood in an arterio-venous (AV) fistula, which is a surgical connection between an artery and a vein that is used for hemodialysis. The user may first need to expose the fistula site and identify the desired location for placing the band 25 around the fistula. The user may then take the free end of the band 25, which has an end of arrowhead shape (arrowhead 27) and lead it around the fistula. The user may then insert the arrowhead 27 into the proximal opening 33 of the tunnel section 89, and then advance the arrowhead 27 until it reaches and connects with the receiver component 19 inside the controller 5. The receiver component 19 is connected to the band adjusting mechanism. The user may change the diameter of the band 25 by turning the adjusting nut 13 in the controller 5. After adjusting the band, the band is secured by engaging a lock 17. The controller 5 may then be disconnected from the band element 3 by cutting across line of cut-off plane 41. This would complete the band installation, adjustment, securing, and disconnection of the controller 5.

The band element 3 of the present invention overcomes the limitations of prior art devices by providing a number of technical advantages listed below:

In the past, users faced challenges due to use of connectors at the end of the band and rigid plastic components, leading to complications and pinching during installation. The present disclosure addresses this by providing a soft polymer band element 3 with no end connectors. This design eliminates the risks associated with implanting rigid components in the body, reducing the potential for tissue damage, vessel wall injury, and complications that were present in the prior art.

Also in the past, the installation of the band required a snap-together connection near the vessel surface, which is cumbersome and risked vessel damage. The present invention eliminates this limitation by providing a simplified and safer installation process. The user may easily lead the arrowhead 27 of the band 25 around the blood vessel 59 and insert it into the tunnel section 89 of the band element. This moves the connection of the band end to inside the controller 5, providing a safer and easier installation.

Also in the past, the installation of the band required a snap-together connection near the vessel surface, which is cumbersome and risked vessel damage. The present invention eliminates this limitation by providing a simplified and safer installation process. The user may easily lead the arrowhead 27 of the band 25 around the blood vessel 59 and insert it into the tunnel section 89 of the band element. This moves the connection of the band end to inside the controller 5, providing a safer and easier installation. The present invention effectively addresses the limitations of prior art through the following modifications:

a. Molding a 1-piece soft polymer band with no hard surfaces;
b. Eliminating the band end connector by molding the end of the band as a connector:
c. Simplifying and improving the safety of the band installation process by using a one-way snap-in design inside the controller instead of near the vessel surface:
e. Eliminating the need for secondary securing:
f. Eliminating vessel pinching during band closure by using a tapered ramp that conforms to the inside surface of the band as the diameter changes: and
g. Eliminating the implantation of adhesive.

Further, the securing means 17 of present invention overcomes the prior art's 675' device limitation of an absolute lock. Unlike the permanent lock of the prior art, the securing means 17 may be designed to allow the band 25 to slip past the lock and open (after having engaged the lock), in response to a pressurized balloon placed inside the blood vessel 59. This dynamic securing mechanism ensures safety and adaptability, enhancing the clinical effectiveness of the device.

Further, in the past, the presence of a fixed rigid plastic component prevented the band from ever being round. The present invention addresses this limitation by introducing a continuously curved band element 3 that is circular over a wide diameter range. This innovative design improves the device's compatibility with different clinical scenarios. Further, the present invention eliminates the need for adhesive implantation. This design of the instant disclosure reduces the introduction of foreign materials and potential complications, enhancing patient safety.

Figure 5A:
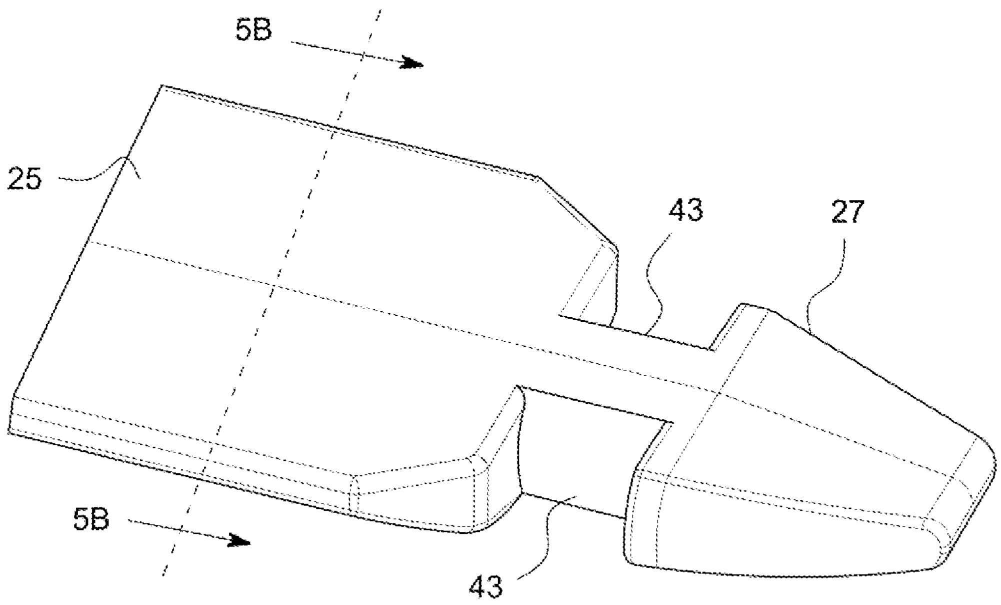
FIG. 5A is a perspective view of an arrowhead end of a band length, in accordance with an embodiment of the present disclosure.

FIG. 5A is a perspective view of the arrowhead 27 of the band 25, in accordance with an embodiment of the present disclosure. FIG. 5A shows the details of the arrowhead 27 of the band 25, which is designed to engage with the receiver component 19 inside the controller 5 as shown by longitudinal direction 6B-6B. The arrowhead 27 may include an arrowhead notch 43 behind the angled front end, which may be used to receive and seat the arm ends 71 of the receiver component 19. The taper of the arrowhead 27 may facilitate both inserting into the proximal opening 33 and the splaying-apart of the receiver arms 69, shown in FIG. 10.

Figure 5B:
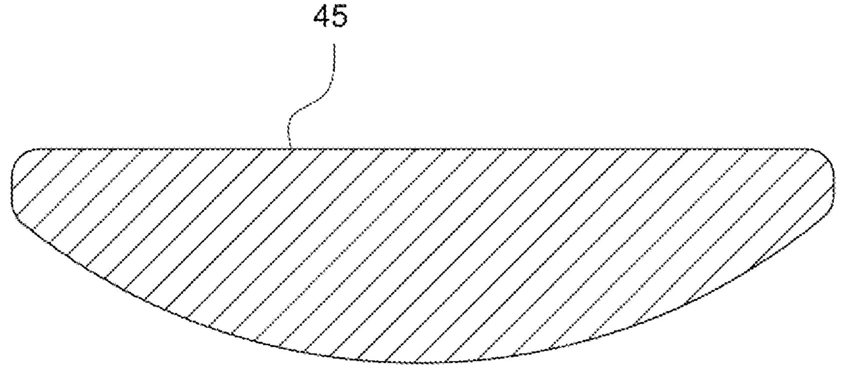
FIG. 5B illustrates a cross-section shape of the band length for producing a saddle-shaped restriction, in accordance with an embodiment of the present disclosure.

FIG. 5B illustrates a cross-section shape of the band 25 for producing a saddle-shaped restriction, in accordance with an embodiment of the present disclosure. FIG. 5B shows an example of a cross-section shape 45 of the band 25 (for example, length of the band 25), which may be used to produce a smooth saddle-shaped restriction in a hollow conduit, such as the blood vessel 59. The cross-section shape 45 may have a curved inner surface and a flat outer surface, or other variations that achieve the same effect. In other words, the configuration shown in present FIG. 5B is just one example, embodies the concept of creating the desired saddle-shaped restriction. However, it should be noted that other variations of the cross-section shape may achieve a similar effect.

Figure 6A:
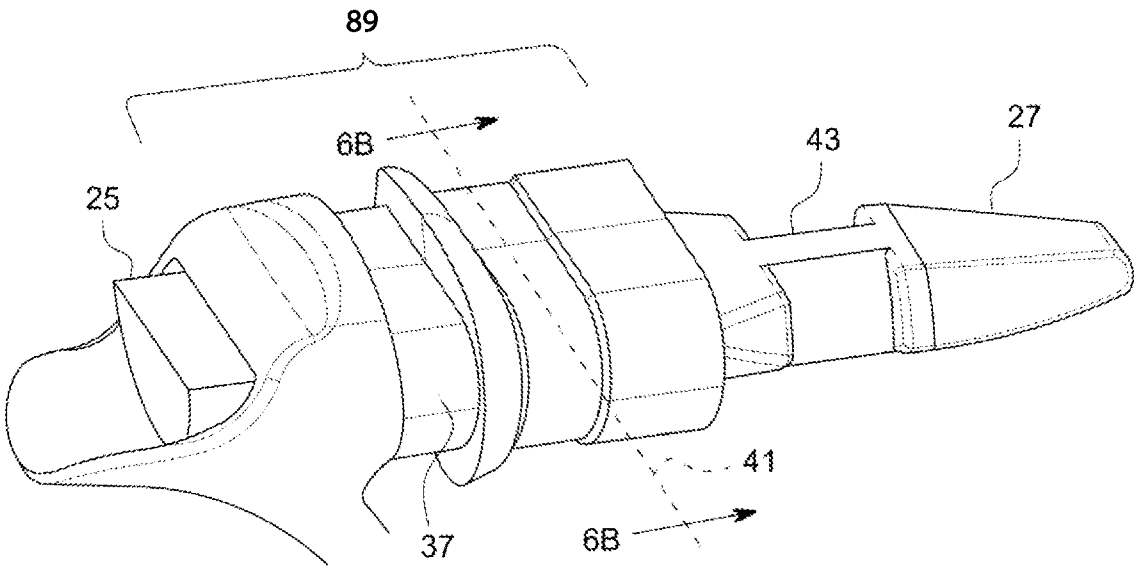
FIG. 6A is a perspective view of a band length passing through and extending past a tunnel section with a cut-off plane intended for disconnecting a controller, in accordance with an embodiment of the present disclosure.

FIG. 6A is a perspective view of a band 25 passing through and extending past the tunnel section 89 of a band element 3, showing cut-off plane 41 intended for disconnecting the controller 5 in longitudinal direction 6B-6B, in accordance with an embodiment of the present disclosure. The cut-off plane 41 may be located in the middle of an area that does not leave any adhesive in the body when cut. This design emphasizes patient safety by preventing any residual adhesive from remaining within the body after the controller 5 is disconnected. Also shown is notch 37, used to locate a securing means to maintain the band diameter after disconnecting the controller 5.

Figure 6B:
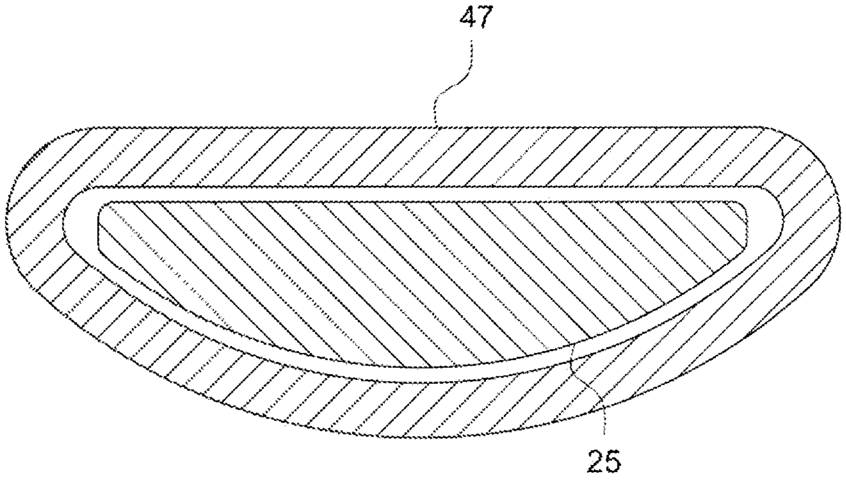
FIG. 6B is a cross-sectional view of the band length at the cut-off plane shown in FIG. 6A, depicting the band length inside the tunnel section, in accordance with an embodiment of the present disclosure.

FIG. 6B is a cross-sectional view of the band 25 at the cut-off plane 41 shown in FIG. 6A, depicting the band 25 inside the tunnel section 89, in accordance with an embodiment of the present disclosure. FIG. 6B shows how the tunnel section 89 surrounds band 25 at the cut-off plane 41. The tunnel section 89 has cross-section shape 47 that reflects the cross-section shape of the band 25, such that the band 25 may slide smoothly through the tunnel section 89.

Figure 7:
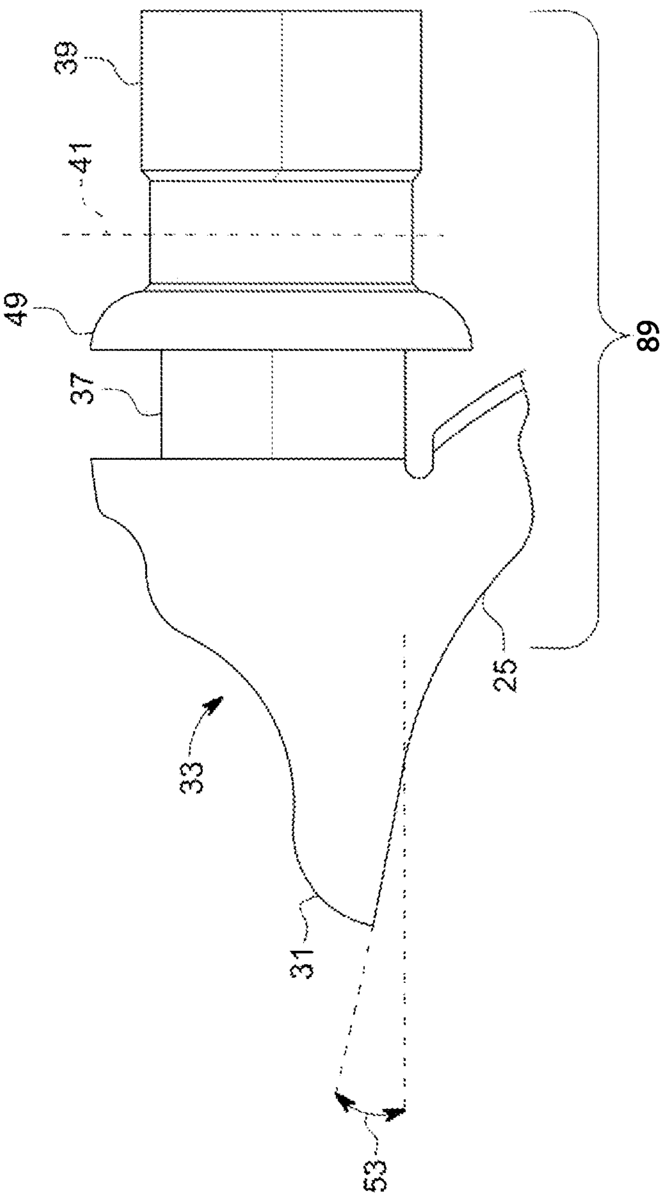
FIG. 7 is a side view of a band element showing the tunnel section and ramp in accordance with an embodiment.

FIG. 7 is a side view of the tunnel section 89 of a band element 3 showing a proximal opening 33, in accordance with an embodiment of the present disclosure. FIG. 7 shows how the ramp 31 extends from the base of the proximal opening 33. The ramp 31 has an upward tilt angle 53, which may allow the ramp 31 to contact the inner surface of the band 25 at larger diameters than if the ramp 31 was parallel to the floor of the tunnel section 89. The ramp 31 may also provide a smooth and tapered stationary element that allows the closing of band 25 to slide up the ramp 31 without pinching the vessel wall. FIG. 7 also shows notch 37 which may be used to locate a securing means, and rib 49 used to keep the securing means within notch 37. Bonding surface 39, is used to connect band element 3 to controller 5.

Figure 8:
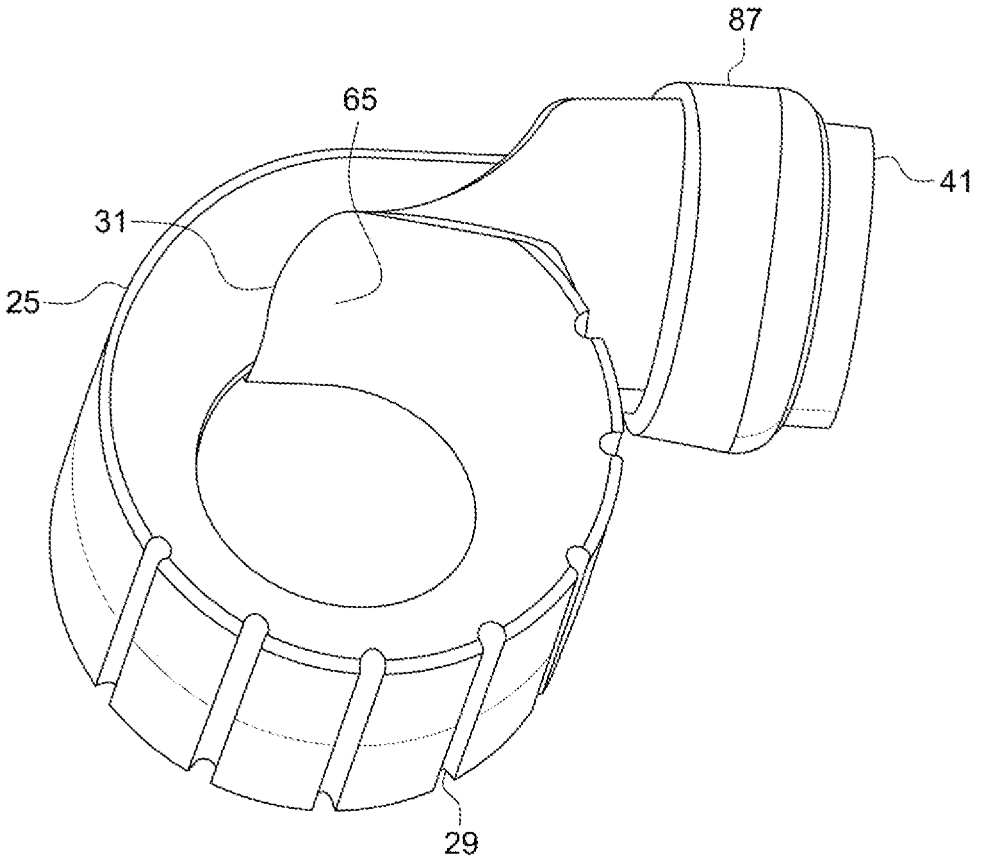
FIG. 8 is a perspective view illustrating conformity of a ramp to an inner surface of the band length in a closed and secured state, in accordance with an embodiment of the present disclosure.

FIG. 8 is a perspective view illustrating conformity of the ramp 31 to the inner surface of the band 25, in accordance with an embodiment of the present disclosure. The ramp 31 is tapered and has a small, soft, radiused edge. FIG. 8 shows how the ramp 31 adapts to the inner surface of the band 25, providing a continuously curved inside shape 65 at all diameters. The tapered ramp 31 is made of a thin, soft, and flexible material that bends to provide a smoothly continuous arc to the closing of band 25. This dynamic adaptation may ensure a harmonious interface between the stationary ramp 31 and the movable band 25, preventing any gap or pinch point between the band 25 and the ramp 31, which may pinch the vessel wall and occlude the vessel. FIG. 8 further illustrates an exemplary locked band 87 after cutting across cut-off plane 41 and disconnecting the controller 5. Also shown in FIG. 8 are rear notches 29 which increase the flexibility of band 25 at smaller diameters, allowing easier closure.

Figure 9:
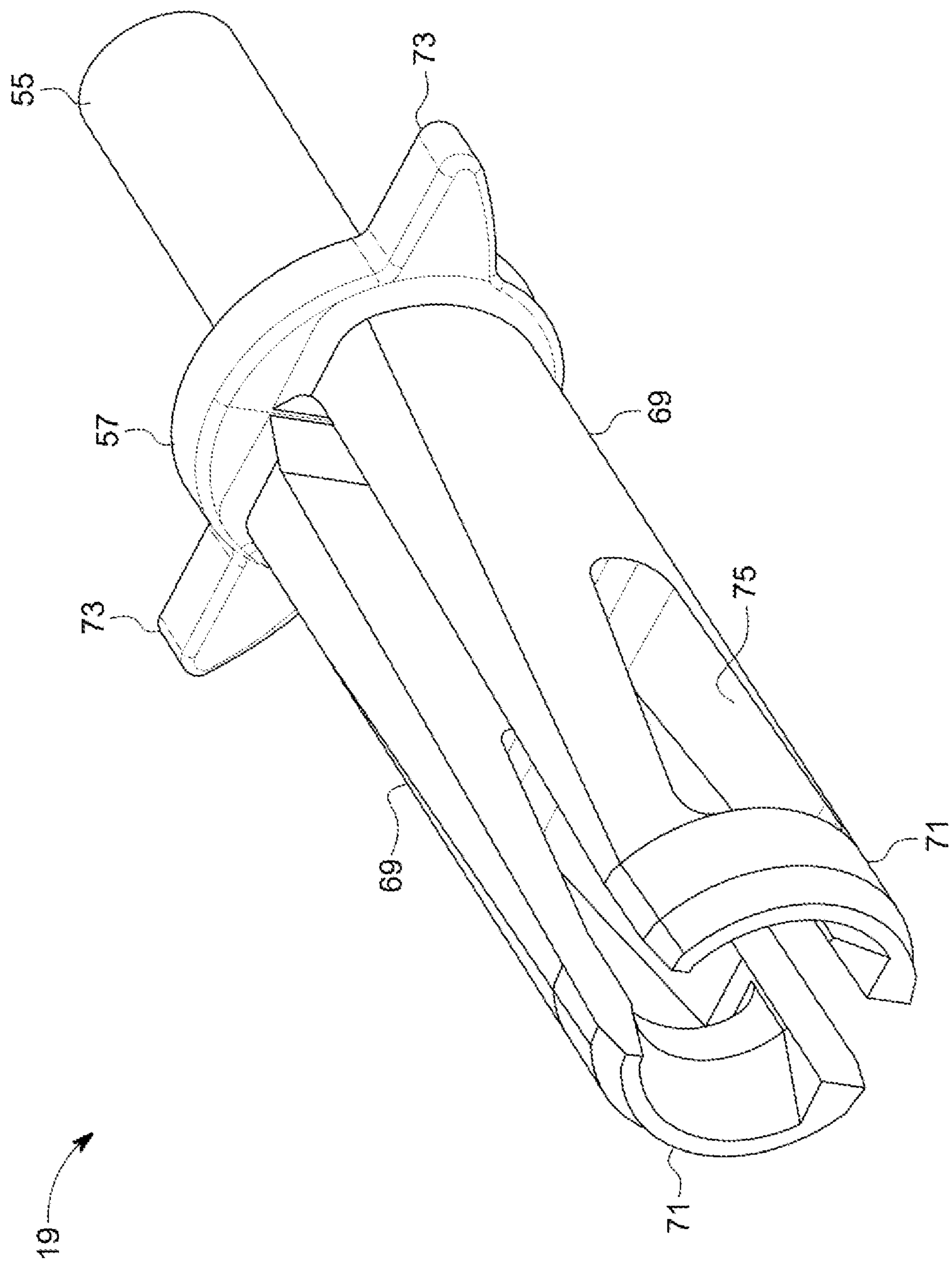
FIG. 9 is a perspective view of a receiver component illustrating the flexible arms used to capture the band end in accordance with an embodiment of the present disclosure.

FIG. 9 is a perspective view of the receiver component 19, which is used to connect the arrowhead 27 of the band 25 to the screw 15 inside the controller 5. The receiver component 19 has two flexible receiver arms 69 that extend from a base 57 and have arm ends 71 that are shaped to engage with the arrowhead notch 43 in the arrowhead 27. The receiver component 19 also has side openings 75 that accommodate the wide aspect of the arrowhead 27. The base 57 has two side extensions or wings 73 that ride inside a channel in the housing 7, shown in FIG. 12*b*, to provide anti-rotation means to the screw 15. The base 57 also has a rear extension 55 that is used to bond the receiver component 19 to the end of the screw 15.

In other words, the receiver component 19 is a two-part system that connects the arrowhead 27 of the band 25 to the screw 15 inside the controller 5. The two flexible receiver arms 69 of the receiver component 19 fit into the arrowhead notch 43 in the arrowhead 27, and the side openings 75 accommodate the wide part of the arrowhead 27. The base 57 of the receiver component 19 has two side extensions, or wings 73, that ride inside a channel in the housing 7 to prevent the screw 15 from rotating.

Figure 10C:
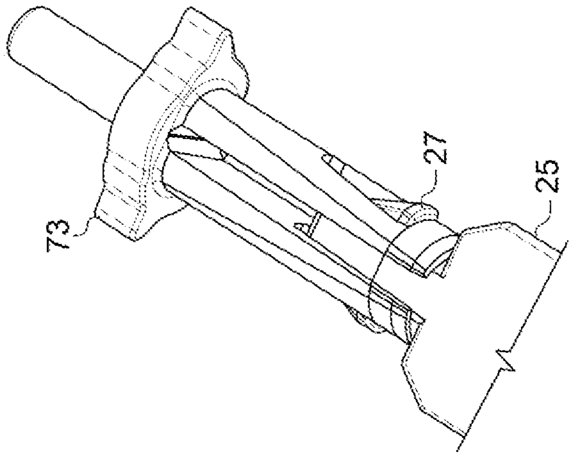
FIGS. 10A-10C is series of perspective views illustrating the sequence involved in the connection of the arrowhead to the receiver component, in accordance with an embodiment of the present disclosure.
Figure 10B:
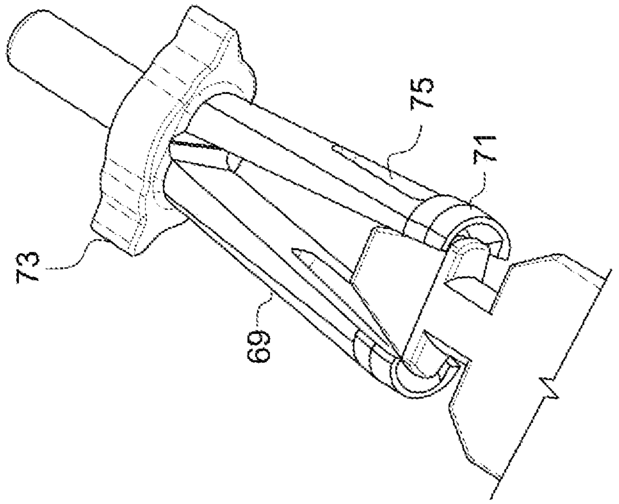
Figure 10A:
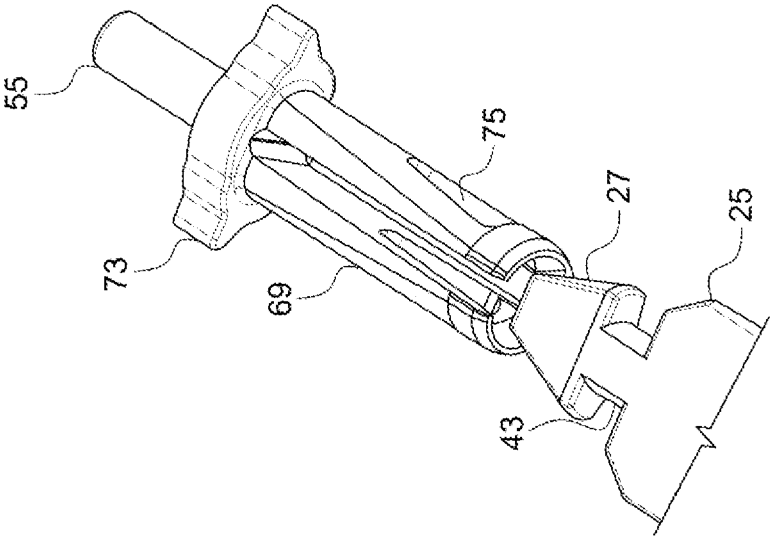

FIGS. 10A-10C is series of perspective views illustrating a sequence involved in the connection of the arrowhead 27 to the receiver component 19, in accordance with an embodiment of the present disclosure. FIG. 10A shows the arrowhead 27 approaching the receiver component 19. As the angled arrowhead 27 moves closer to the receiver component 19, it is positioned to spread the receiver arms 69 of the receiver component 19.

FIG. 10B shows how the arrowhead 27 continuing its advancement, elastically spreads the receiver arms 69 of the receiver component 19. The design of the arrowhead 27 facilitates this spreading motion by exerting outward force on the receiver arms 69. This elastic spreading is an integral part of achieving a secure and reliable connection.

FIG. 10C shows how, after further advancing the arrowhead 27, the arm ends 71 (e.g., two-receiver arm ends) drop into the arrowhead notch 43, securing the connection to band 25. In this final stage of the sequence, the connection of the arrowhead 27 to the receiver component 19 is completed. This one-way engagement securely locks the band 25 in place, and provides a strong push/pull capability to the controller 5. At this point, the device reaches a stable state where the band 25 is in its maximum diameter position, forming a loop around the hollow conduit. This position is also shown as FIG. 11*b*.

Figure 11A:
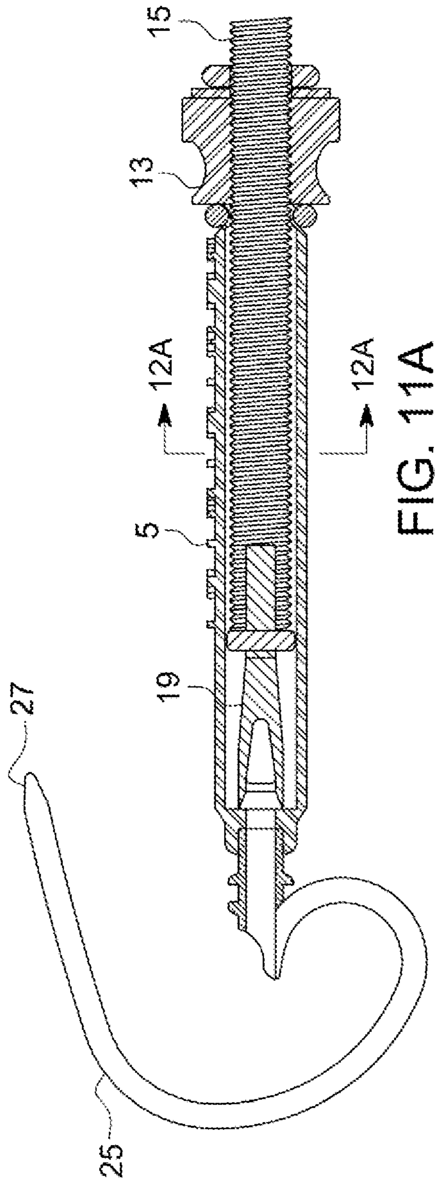
FIGS. 11A-11C is a series of longitudinal cross-sectional views of the device illustrating the process of a band being drawn into the controller as the band is reduced in diameter, in accordance with an embodiment of the present disclosure, in accordance with an embodiment.
Figure 11B:
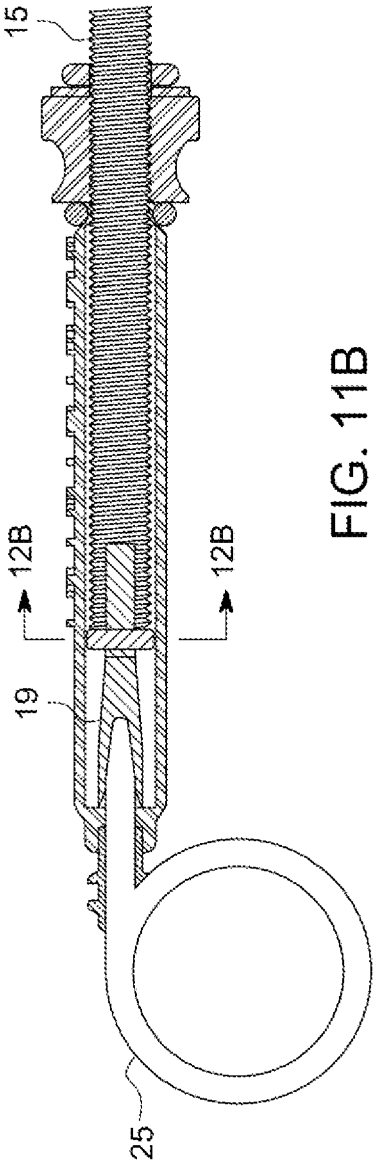
Figure 11C:
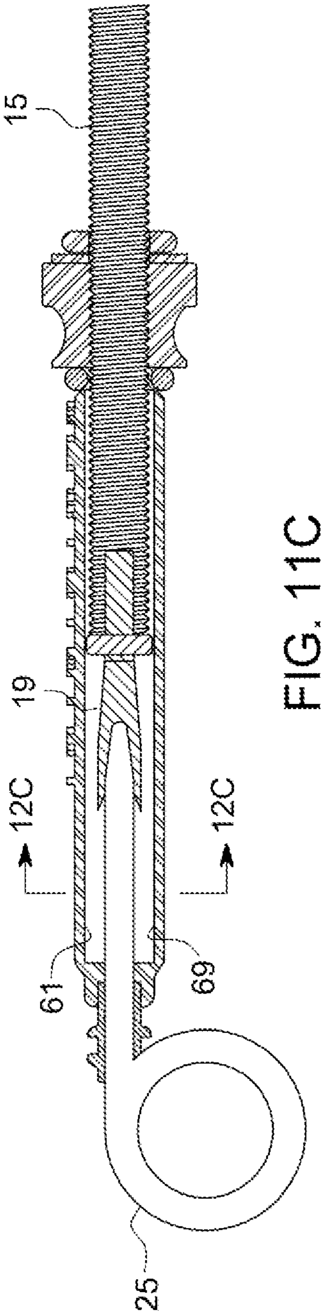

FIGS. 11A-11C is a series of longitudinal cross-sectional views of the precision-controlled conduit restriction device 1 illustrating the process whereby band 25 is drawn into the controller 5 as the band 25 closes, in accordance with an embodiment of the present disclosure. FIG. 11A shows the precision-controlled conduit restriction device 1 as produced, with the band 25 free to be led around a blood vessel 59. At this stage, the precision-controlled conduit restriction device 1 is shown with the band 25 in a free state, unsecured and ready to be led around the hollow conduit, represented as a blood vessel 59.

FIG. 11B shows the precision-controlled conduit restriction device 1 when arrowhead 27 is first connected to the receiver component 19. This position represents the fully-open state of the band 25. The precision-controlled conduit restriction device 1 is in the state just after the successful connection of the arrowhead 27 to the receiver component 19.

FIG. 11C shows the band 25 in a reduced diameter position. The band 25 has been drawn into the controller 5 through the adjusting mechanism, and both the receiver component 19 and the screw 15 are correspondingly displaced to the right, extending the screw 15 out of the back of the controller 5. This sequence visually captures the mechanism through which the precision-controlled conduit restriction device 1 achieves the desired level of restriction.

Figure 12A:
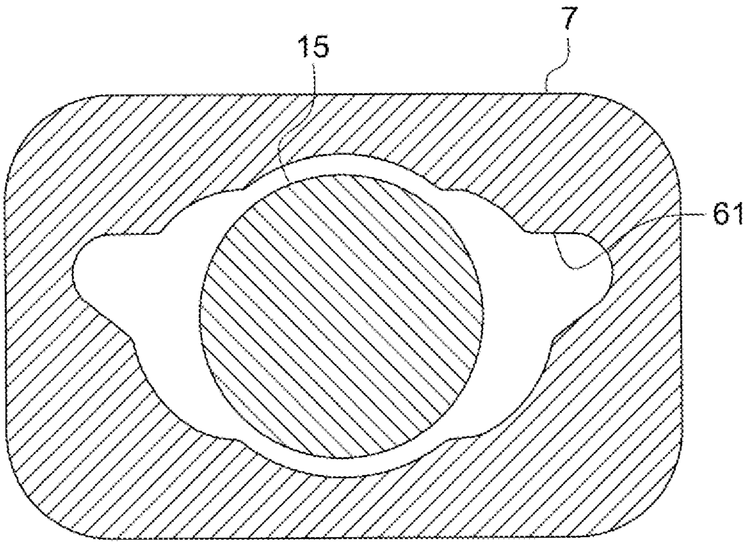
FIGS. 12A-12C depict a series of cross-sectional views through a controller housing, illustrating the internal channel designed to selectively constrain and permit the passage of the band, receiver component, and screw through the housing, in accordance with an embodiment of the present disclosure.
Figure 12B:
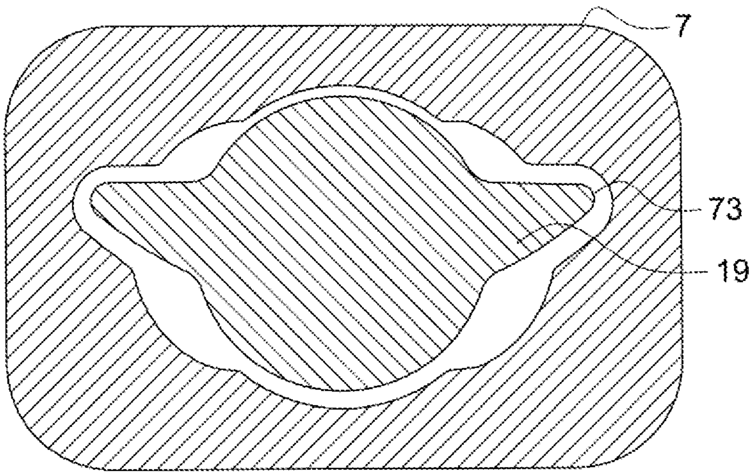
Figure 12C:
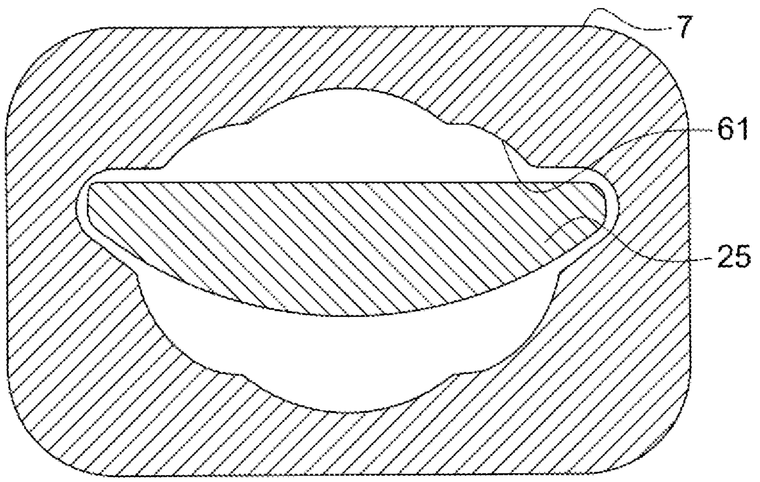

In FIGS. 12A-12C, the focus shifts to the internal workings of the precision-controlled conduit restriction device 1, specifically the housing 7. FIGS. 12A-12C depict a series of cross-sectional views through the housing 7, as defined in FIG. 11A-11C. Internal channel wall 61 is shaped to constrain and permit the passage of the band 25, receiver component 19, and screw 15 through the housing 7, in accordance with an embodiment of the present disclosure. The internal channel wall 61 allows the passage of these components without interfering with their movement or function. FIG. 12A shows how the screw 15 is constrained by internal channel wall 61. FIG. 12B shows how receiver component 19 is constrained by the internal channel wall 61. The wings 73 of the receiver component 19 are constrained by the internal channel wall 61, thereby providing anti-rotation means to the screw 15. Internal channel wall 61 orients receiver component 19 ensuring its proper alignment to connect to arrowhead 27. FIG. 12C illustrates how band 25 is constrained by internal channel wall 61. FIG. 12 serves to highlight the dynamic functionality of the internal channel wall 61 in facilitating the smooth and effective operation of the controlled restriction mechanism.

Figure 13A:
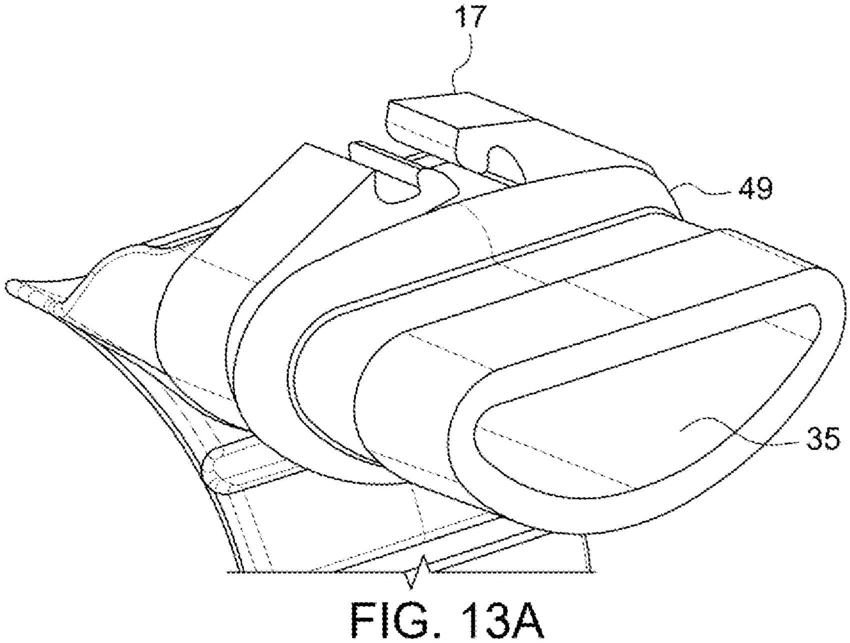
FIGS. 13A-13C depict a series of perspective views of a securing means showing different stages and aspects of its functionality, in accordance with an embodiment of the present disclosure.
Figure 13B:
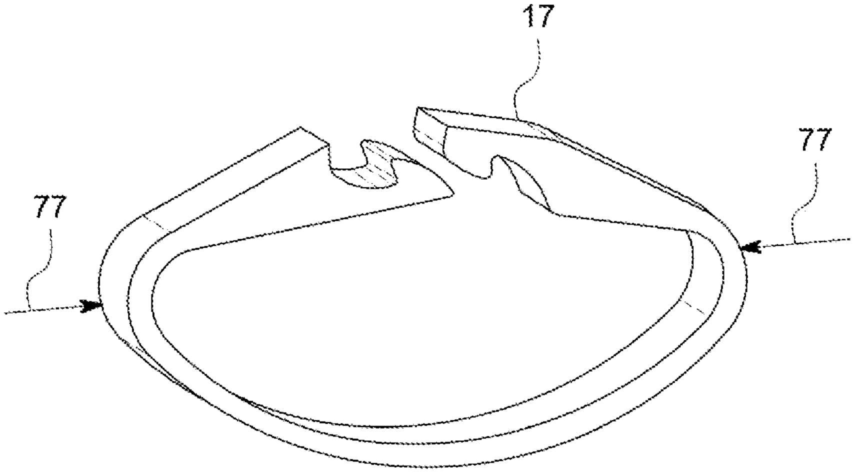
Figure 13C:
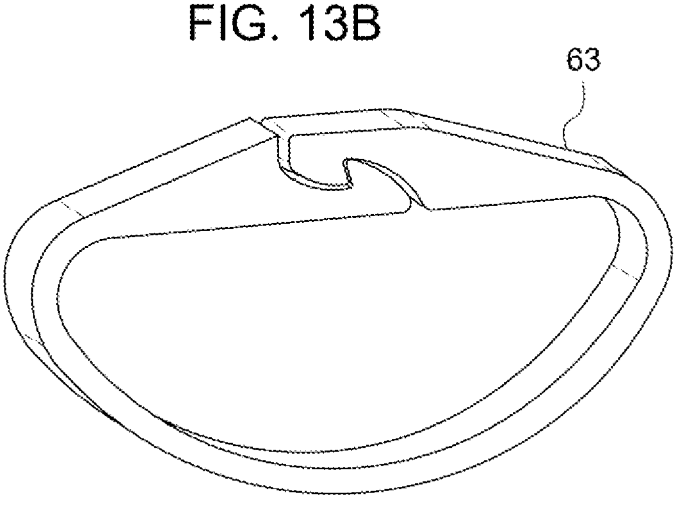

FIGS. 13A-13C depict a series of perspective views of a securing means 17 showcasing different stages and aspects of its functionality, in accordance with an embodiment of the present disclosure. FIG. 13A shows the securing means 17 in the open or unlocked position mounted in the notch 37 and retained by the rib 49. The primary purpose of the securing means 17 is to compress the tunnel section 89 over the band 25, thereby preventing movement of the band 25.

FIG. 13B provides a closer look at the securing means 17 in the open position. This view shows the securing means 17 in an open position, with arrows 77 indicating the location for pinching the sides of the securing means 17 to close or lock. The positioning of arrows 77 indicates the specific locations where pressure can be applied to pinch the sides of the securing means 17 together. This action is what eventually enables the securing means 17 to transition from an open to a locked state 63, effectively securing the band 25 in place.

FIG. 13C shows the securing means 17 (for example, a securing means lock) in a closed or locked state 63. In this state, the securing means 17 compresses the tunnel section 89 over the band thereby preventing movement of the band. The securing means 17 may be designed to allow the band 25 to slip past lock 17 in response to a high pressure intraluminal balloon inserted inside the blood vessel 59.

In one embodiment, the securing means 17, implemented as a click-together design, may be placed around the tunnel section of band element 3 to compress the tunnel section over the band 25. The degree of compression may be precisely controlled by the shape of the inside curve of the locking mechanism.

Fabrication of the securing means 17 may be performed using electrical discharge machining (EDM), utilizing materials such as 0.062" thick titanium sheet. The two-dimensional and digital nature of the securing means is instrumental in achieving its intricate design. The degree of tunnel compression may be finely controlled by altering the inside shape of the securing means, which is conveniently performed in a two-dimensional CAD environment, then translated into a cutting path.

In another preferred embodiment, the band element 3 may incorporate a strategically designed weak point that allows the band to break or stretch open in response to an angioplasty balloon.

The securing (e.g., lock) of the band element 3 may be achieved through various design means, all of which yield a similar clinical outcome, ensuring controlled and secure band engagement.

Figure 14:
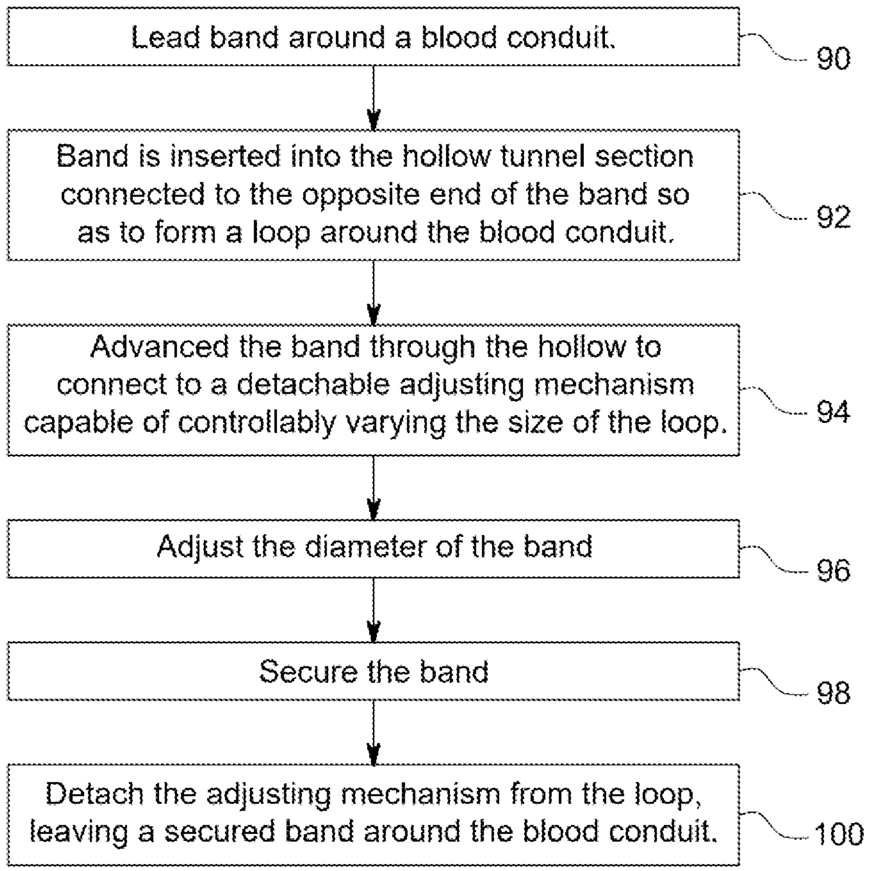
FIG. 14 is a flow-chart representation of a method according to the present invention.

FIG. 14 is a flow-chart representation of a method according to the present invention. The method is based upon having a length of band, wherein one end is attached to a hollow section. The hollow section is designed to allow passage of the band. One end of the hollow section is designed for insertion of the band end, and the other is removably attached to a mechanism capable of controllably moving the band through the tunnel.

In block 90, the free end of a band is led around a blood conduit. The band may be shaped to facilitate this process.

In block 92, the end of the band is inserted into the hollow section attached to the opposite end of the band. The band then forms a loop around the blood conduit.

In block 94, the band is advanced through the hollow section to connect to a detachable mechanism, connected to the opposite end of the tunnel section, capable of varying the diameter of the band loop around the blood conduit.

In block 96, the band adjusting means of the mechanism is employed to change the diameter of the band.

In block 98, after adjustment, the band diameter is secured by activating securing means to prevent the band from opening under normal clinical conditions.

In block 100, after securing the band diameter, the adjusting mechanism is detached from the tunnel section, leaving the secured band around the blood conduit.

As will be appreciated by those skilled in the art, the techniques described in the various embodiments discussed above are not routine, or conventional or well understood in the art. The techniques discussed above may provide several advantages over the prior art for controlling the flow of fluid in the hollow conduit, such as the blood vessel 59. Some of the advantages are as follows: the precision-controlled conduit restriction device 1 of the present invention is easy to install and adjust, without requiring any complex or delicate manipulation of small parts in a surgical field. Further, the precision-controlled conduit restriction device 1 is safe, without using any hard or sharp components that could damage or pinch the vessel wall. Further, the precision-controlled conduit restriction device 1 does not require any secondary securing of the band element 3. Furthermore, the precision-controlled conduit restriction device 1 is versatile and adaptable, without having any fixed or rigid elements that prevent the band element 3 from being circular or conforming to the vessel shape.

In light of the above-mentioned advantages and the technical advancements provided by the disclosed method and system, the claimed steps as discussed above are not routine, conventional, or well understood in the art, as the claimed steps enable solutions to the existing problems in conventional technologies. Further, the claimed steps clearly bring an improvement in the functioning of the precision-controlled conduit restriction device 1 itself as the claimed steps provide a technical solution to a technical problem.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide illustrative examples of the principles of this invention and its practical application to thereby enable one of ordinary skill in the art to utilize the invention in various embodiments and with various modifications as are suited to the particular use contemplated.

While various embodiments have been described above, it should be understood that they have been presented by way of example only, and not limitation. Thus, the breadth and scope of the present disclosure should not be limited by any of the above-described exemplary embodiments, but should be defined only in accordance with the following claims and their equivalents.

What is claimed is:

1. A device for providing controlled restriction of a hollow conduit in a body, the device comprising: a molded polymer band element having an integrally formed tunnel section with a proximal opening and a distal opening, a length of the band element extending from the proximal opening, a controller removably attached to the distal opening, comprising a mechanism for adjusting a diameter of a loop formed by the length of the band element, wherein an integral connector at a free end of the length of the band element is insertable through the proximal opening to form a loop around the hollow conduit, and wherein the integral connector is advanced through the tunnel section and into the controller to permanently engage with the mechanism for adjusting the diameter of the loop, a securing means to fix the loop diameter after adjustment, and a means to disconnect the controller from the band element after securing, leaving the band element and the securing means around the hollow conduit.

2. The device of claim 1, wherein the controller is disconnected by cutting a short segment of the band element between the controller and the securing means so as to leave the band element secured around the hollow conduit.

3. The device of claim 1, wherein the band element is radiopaque.

4. The device of claim 1, wherein the length of the band element has a circular cross section, a rectangular cross section, or is shaped to provide a specifically-shaped restriction.

5. The device of claim 1, wherein the mechanism for adjusting the diameter of the loop comprises a captured nut that linearly moves a threaded rod connected to the free end of the length of the band element thereby drawing the length of the band element into the controller.

6. The device of claim 1, wherein the securing means is a lock that compresses the tunnel section over a section of the length of the band element to produce a controlled resistance to movement of the length of the band element which maintains the diameter of the loop under normal clinical conditions, and allows the band element to open from its secured state in response to a pressurized balloon placed inside the hollow conduit.

7. The device of claim 1, wherein the controller further comprises an indicator for displaying the diameter of the loop.

8. The device of claim 1, wherein the tunnel section further comprises a tapered ramp element extending from a base of the proximal opening and conforming to an inner surface of the loop.

9. The device of claim 1, wherein the securing means comprises a clamp that compresses the tunnel section over a length of the band element to create a frictional lock.

10. The device of claim 1, wherein the integral connector is shaped as an arrowhead.

11. A method to controllably reduce the flow in a blood conduit using the device of claim 1, the method comprising the steps of: leading the free end of the band element around a blood conduit; inserting the free end of the band element into the tunnel section connected to the opposite end of the band element so as to form the loop around the blood conduit; advancing the band element through the tunnel section to connect to the controller; adjusting a diameter of the loop using the mechanism for adjusting the diameter of the loop; securing the band element; and detaching the controller from the hollow section so as to leave the secured band element in place around the blood conduit.

12. A device for providing controlled restriction of a hollow conduit in a body, the device comprising: a molded polymer band element having an integrally formed tunnel section with a proximal opening and a distal opening, a length of the band element extending from the proximal opening, a controller removably attached to the distal opening, comprising a mechanism for adjusting a diameter of a loop formed by the length of the band element, wherein an integral connector at a free end of the length of the band element is insertable through the proximal opening to form a loop around the hollow conduit, and wherein the integral connector is advanced through the tunnel section and into the controller to permanently engage with the adjusting mechanism, a securing means located inside the tunnel section to secure the diameter of the loop, and a means to disconnect the controller from the band element, leaving the band element and securing means around the hollow conduit.

13. The device of claim 12, wherein the band element is secured using a detent-type mechanism within the tunnel section, wherein periodically spaced elements along the length of the band element engage with a fixed complementary geometry inside the tunnel section.

14. The device of claim 12, wherein the band element is secured by creating a friction-fit between the band element and the tunnel section, and wherein the controller is a disposable or a reusable controller.

15. The device of claim 12, wherein the securing means is a lock that produces a controlled resistance to band movement of the length of the band element that maintains the diameter of the loop under normal clinical conditions, and allows the band to open from its secured state in response to a pressurized balloon placed inside the hollow conduit.

16. The device of claim 15, wherein the controller is disconnected from the band element by cutting a short segment of the band element between the controller and the securing means so as to leave the band element secured around the hollow conduit.

* * * * *